United States Patent [19]

Bansho et al.

[11] Patent Number: 5,275,956
[45] Date of Patent: Jan. 4, 1994

[54] METHOD OF MEASURING CONCENTRATION OF ORGANIC CHLORINE COMPOUND BY CHEMILUMINESCENCE

[75] Inventors: Kenji Bansho; Hiroaki Tao; Akira Miyazaki; Takashi Imagawa, all of Tsukuba, Japan

[73] Assignee: Director-General of Agency of Industrial Science and Technology, Japan

[21] Appl. No.: 978,356

[22] Filed: Nov. 18, 1992

[30] Foreign Application Priority Data

Feb. 5, 1992 [JP] Japan .................. 4-54274

[51] Int. Cl.$^5$ .................. G01N 21/76
[52] U.S. Cl. .................. 436/125; 436/124; 436/126; 436/160; 436/172; 422/52
[58] Field of Search .......... 436/124, 125, 160, 172, 436/126; 422/52

[56] References Cited

U.S. PATENT DOCUMENTS

| | | | |
|---|---|---|---|
| 3,287,089 | 11/1966 | Wilburn | 422/52 |
| 4,231,754 | 11/1980 | Vogelhut | 422/52 |
| 4,401,763 | 8/1983 | Itoh | 436/124 |

FOREIGN PATENT DOCUMENTS

| | | |
|---|---|---|
| 55-096453 | 7/1980 | Japan . |
| 0789385 | 12/1980 | U.S.S.R. . |
| 0923271 | 10/1982 | U.S.S.R. . |

*Primary Examiner*—James C. Housel
*Assistant Examiner*—Jan M. Ludlow
*Attorney, Agent, or Firm*—Lorusso & Loud

[57] ABSTRACT

The concentration of an organic chlorine compound contained in a gaseous medium is measured in situ by feeding the gaseous medium to a reaction zone and oxidizing the chlorine compound to produce a reactive gas capable of reacting with a chemiluminescent compound to cause chemiluminescence. The reactive gas is contacted with the chemiluminescent compound contained in a cell to cause chemiluminescence whose intensity is proportional to the amount of the reactive gas produced by the oxidation of the organic compound. The concentration of an organic chlorine compound contained in an aqueous medium may also be measured by the similar method after separating the organic chlorine compound as vapors from the aqueous medium. A device suitable for the above measurement is also disclosed.

4 Claims, 6 Drawing Sheets

5,275,956

METHOD OF MEASURING CONCENTRATION OF ORGANIC CHLORINE COMPOUND BY CHEMILUMINESCENCE

BACKGROUND OF THE INVENTION

This invention relates to a method of measuring the concentration of an organic chlorine compound contained in an atmosphere or an aqueous medium and to a device useful for carrying out the method.

Hitherto, chlorine compounds contained in an atmosphere or an aqueous medium, such as a waste gas or waste water, have been analyzed by gas chromatography. Thus, it is necessary to perform the analysis at a place different from the place where the samples are collected.

SUMMARY OF THE INVENTION

It is an object of the present invention to provide a method which can measure, in situ, the concentration of organic chlorine compounds with a high sensitivity.

Another object of the present invention is to provide a simple device suitable for the in situ measurement of organic chlorine compounds.

In accomplishing the above object, there is provided in accordance with the present invention a method of measuring the concentration of an organic chlorine compound contained in an atmosphere, comprising the steps of:

feeding the atmosphere to a reaction zone at a predetermined feed rate and oxidizing the chlorine compound fed to the reaction zone to produce a reactive gas capable of reacting with a chemiluminescent compound to cause chemiluminescence;

introducing the reactive gas produced in the reaction zone into a cell containing the chemiluminescent compound to bring the reactive gas into contact with the chemiluminescent compound and thereby to cause chemiluminescence; and detecting the intensity of the chemiluminescence in the cell.

In another aspect, the present invention provides a method of measuring the concentration of an organic chlorine compound contained in an aqueous medium, comprising the steps of:

vaporizing the organic chlorine compound and causing the vapors of the organic chlorine compound to pass through a gas permeable membrane, thereby to separate the organic chlorine compound from the aqueous medium;

feeding the separated organic chlorine compound to an oxidizing zone and oxidizing the organic chlorine compound fed to the reaction zone to produce a reactive gas capable of reacting with a chemiluminescent compound to cause chemiluminescence;

introducing the reactive gas produced in the reaction zone into a cell containing the chemiluminescent compound to bring the reactive gas into contact with the chemiluminescent compound and thereby to cause chemiluminescence; and detecting the intensity of the chemiluminescence in the cell.

The present invention also provides a device for measuring the concentration of an organic chlorine compound contained in an atmosphere, comprising:

an oxidizing zone for decomposing the chlorine compound to form a reactive gas capable of reacting with a chemiluminescent compound to cause chemiluminescence;

a cell connected to the oxidizing zone and containing the chemiluminescent compound;

a detector for detecting the intensity of the chemiluminescence in the cell; and means for passing the atmosphere through the oxidizing zone to the cell.

In a still further aspect, the present invention provides a device for measuring the concentration of an organic chlorine compound contained in an aqueous medium, comprising: separating means having a gas permeable membrane for separating the organic chlorine compound as vapors from the aqueous medium;

an oxidizing zone connected to the separating means for decomposing the vaporized chlorine compound to produce a reactive gas capable of reacting with a chemiluminescent compound to cause chemiluminescence;

a cell connected to the oxidizing zone and containing the chemiluminescent compound; and a detector for detecting the intensity of the chemiluminescence in the cell.

BRIEF DESCRIPTION OF THE DRAWINGS

Other objects, features and advantages of the present invention will become apparent from the detailed description of the preferred embodiments which follow, when considered in light of the accompanying drawings in which.

DETAILED DESCRIPTION OF THE PREFERRED EMBODIMENTS OF THE INVENTION

Figure 1:
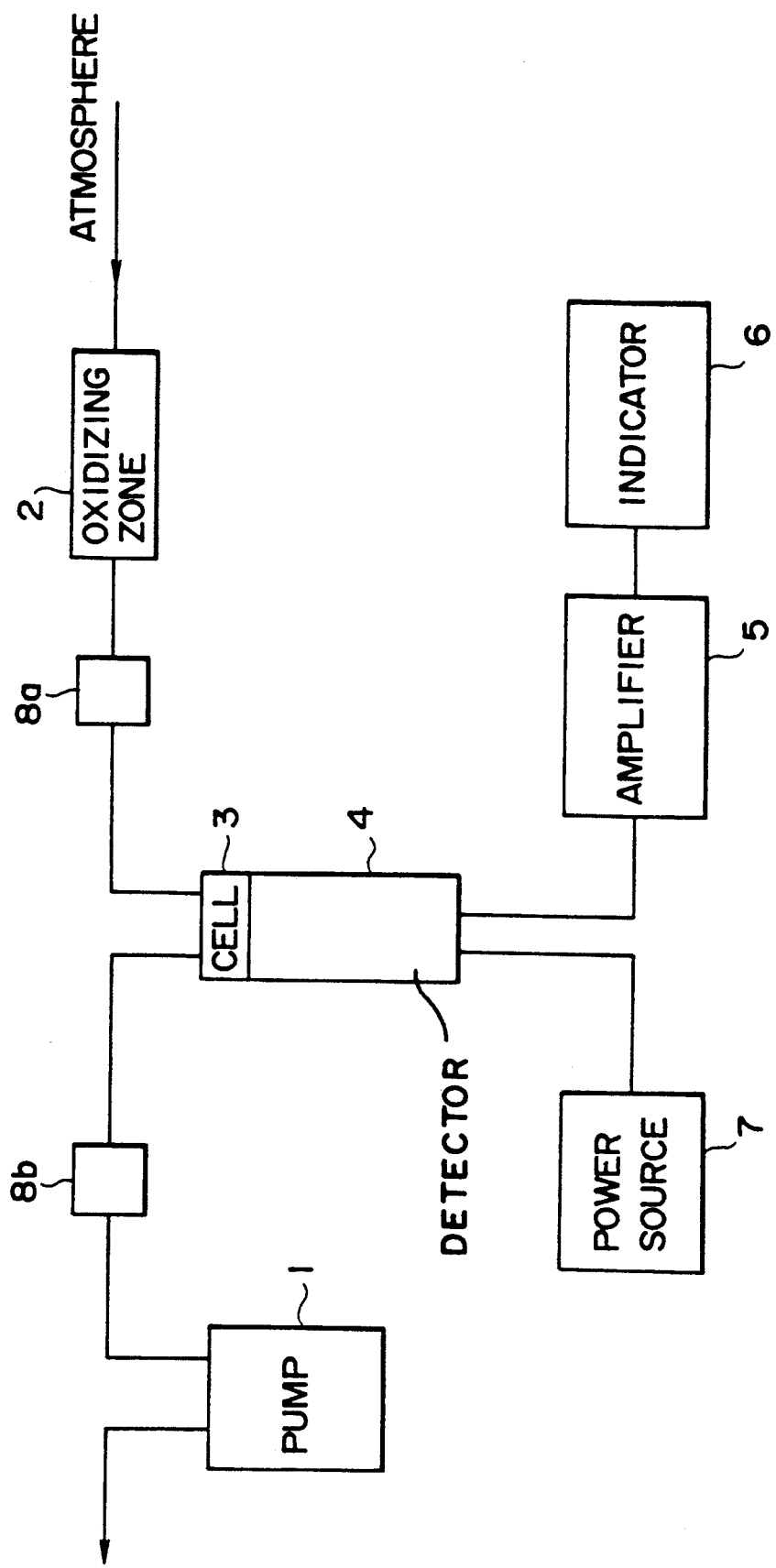
FIG. 1 is a schematic representation of one embodiment of an apparatus according to the present invention.

FIG. 1 depicts a device suitable for carrying out the measurement of the concentration of an organic chlorine compound contained in an atmosphere, such as a waste gas.

Designated as 2 is an oxidizing zone to which the atmosphere to be measured is fed at a predetermined rate and is oxidized to produce a reactive gas. The oxidizing of the chlorine compound is effected by contacting the atmosphere with an oxidizing agent such as (1) a mixture of $H_2SO_4$ with $KMnO_4$ or a mixture of $H_2SO_4$ with $PbO_2$, (2) a mixture of $H_2SO_4$ with $NaNO_3$ or a mixture of $H_2SO_4$ with $HNO_3$ or (3) a mixture of $H_2SO_4$ with $PbO_2$ and $NaNO_3$ or a mixture of $H_2SO_4$ with $PbO_2$ and $HNO_3$ When the oxidizing agent exemplified in (1) above is used, the oxidation of the organic chlorine compound produces molecular chlorine as the reactive gas. In the case of the oxidizing agent (2), there is produced $NO_2$ as the reactive gas. When the compound exemplified in (3) above are used as the oxidizing agent, both molecular chlorine and $NO_2$ are produced as a result of the oxidation of the organic chlorine compound. The use of nitrate ion-containing oxidizing agent such as the compound (2) and (3) is advantageous because $NO_2$ causes high intensity chemiluminescence of a chemiluminescent compound which will be described hereinafter.

When the oxidizing agent is a liquid, a suitable porous support such as fibers or particles of a glass or a ceramic may be used for supporting the oxidizing agent. Such a supported oxidizing agent may be prepared by, for example, immersing the porous support in an aqueous emulsion containing $PbO_2$ and $Pb(NO_3)_2$, followed by drying dried at about 100° C. and impregnation with concentrated sulfuric acid. Impregnation of the porous support with nitrate ion-containing concentrated sulfuric acid may also give a suitable supported oxidizing agent.

The oxidization of the chlorine compound may be also effected by contacting the atmosphere with a platinum filament in the presence of oxygen at a temperature sufficient to oxidize the chlorine compound and thereby to form molecular chlorine. The platinum filament is heated by being connected to a power source such as a battery.

A cell 3 is disposed for fluid communication with the reaction zone 2. The cell contains a chemiluminescent compound capable of causing chemiluminescence upon being contacted with the reactive gas (generally chlorine gas (molecular chlorine) and/or nitrogen dioxide) produced in the oxidizing zone 2. Examples of suitable chemiluminescent compounds include luminol and lucigenin. Especially high sensitivity is obtainable by using an aqueous solution containing 0.005M of luminol and 0.02M of hydrogen peroxide and having a pH of 8.5.

When the reactive gas produced in the oxidizing zone 2 is introduced into the cell 3, the chemiluminescent compound emits light whose intensity is proportional to the amount of the reactive gas produced in the oxidizing zone 2 and fed to the cell 3.

Disposed adjacent to the cell 3 is a detector, preferably a photomultiplier, for detecting the intensity of the light emitted in the cell 3. The photomultiplier 4 is impressed with a high voltage by a power source 7 and generates an electrical current upon receipt of light from the cell 3. The electrical current is amplified by an amplifier 5 and is indicated in an indicator 6.

The reference numeral 1 denotes a suction pump for introducing the atmosphere to be measured into the oxidization zone and for passing the intake atmosphere through the cell. Designated as 8a and 8b are light shielding means for preventing the cell 3 from being exposed to undesirable light such as external light or light emitted from the platinum filament. The shielding means 8a and 8b may be each composed of a black plate and an optical filter.

Figure 2:
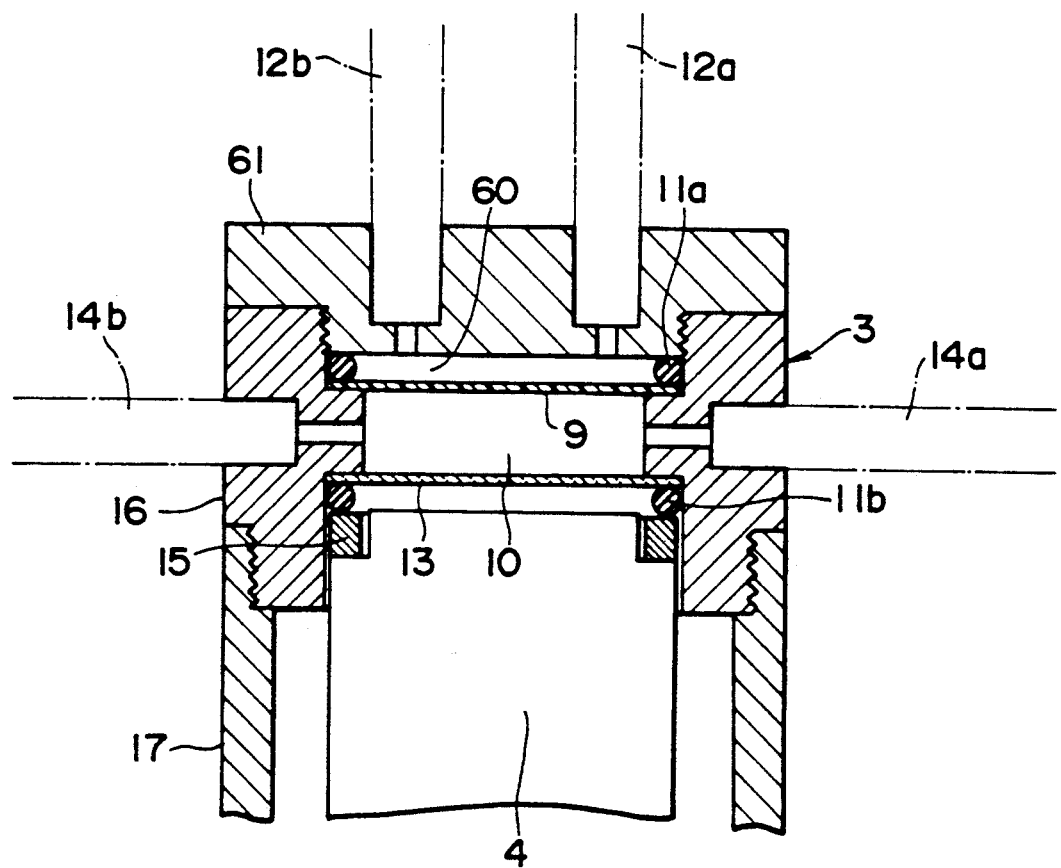
FIG. 2 is an enlarged, fragmentary, vertical, cross-sectional view showing the essential part of the apparatus of FIG. 1.

FIG. 2 shows a structure of the cell 3 and the detector 4. Designated as 17 is a tubular housing within which the photomultiplier 4 is secured. The cell 3 has a tubular main body 16 threadedly connected to the top of the housing 17. Disposed within the main body 16 are a lower glass plate 13 and an upper gas permeable membrane 9 which are spaced apart from each other to define a cell chamber 10 therebetween. A solution containing the chemiluminescent compound is contained in the chamber 10. The main body 16 is provided with inlet and outlet ports 14a and 14b for replacing the used solution in the chamber 10 with a fresh solution. As the membrane 9 there may be suitably used a polytetrafluoroethane resin sheet which permits a gas to pass therethrough but prevents a liquid from passing therethrough.

A cover plate 61 is threadedly connected to the top of the cell main body 16 to define a space 60 between the membrane 9 and the lower surface of the cover plate 61. The cover plate 61 is provided with inlet and outlet ports 12a and 12b which are in fluid communication with the space 60. The inlet port is connected to the oxidizing zone 2 (FIG. 1).

As a result of the above construction, the reactive gas produced in the oxidizing zone 2 is fed to the space 60 and penetrates through the membrane 9 into the chemiluminescent solution in the chamber 10 to cause chemiluminescence of the solution. The light thus emitted passes through the glass plate 13 and is detected by the photomultiplier 4. In FIG. 2, the reference numerals 11a and 11b designate rubber O-rings and the reference numeral 15 designates a metal O-ring.

The present invention is also applied for measuring the concentration of an organic chlorine compound contained in an aqueous medium, such as a waste water. In this case, the organic chlorine compound in the aqueous medium is separated therefrom by being vaporized and passed through a gas permeable membrane.

Figure 3:
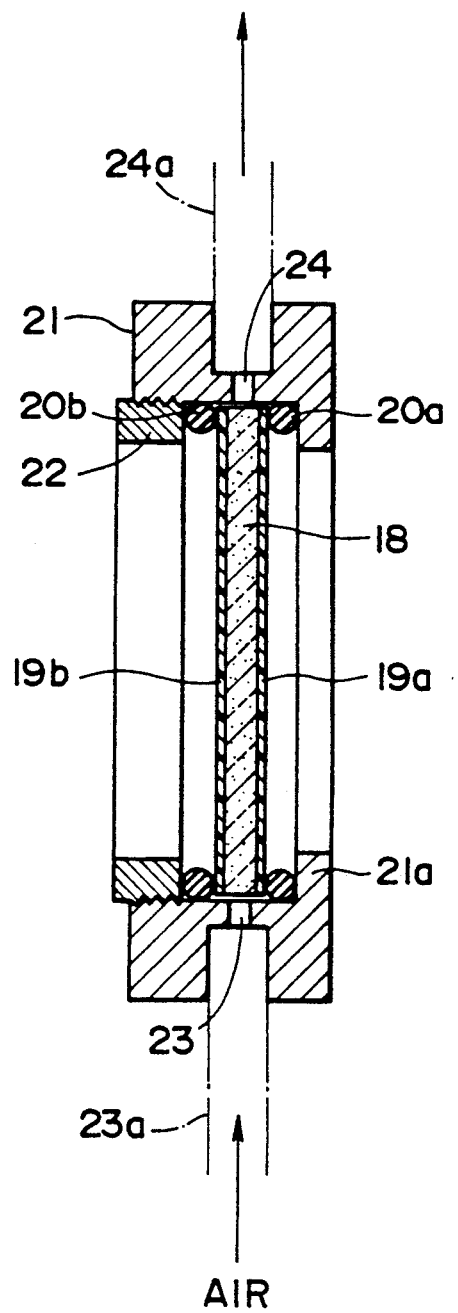
FIG. 3 is a fragmentary, cross-sectional view showing separation means of another embodiment of the present invention.

FIG. 3 depicts one embodiment of such separating means for separating the organic chlorine compound as vapors from the aqueous medium. Designated as 21 is an annular holder having a radially inwardly extending support portion 21a adapted to receive a vapor separating member. The separating member is composed of a rigid, porous, gas permeable disc 18 and a pair of gas permeable membranes 19a and 19b provided on both sides thereof. The separating member is fixed in position between the support portion 21a of the holder 21 and a fixing ring 22 which is threadingly engaged with an inside periphery of the holder 21. Designated as 20a and 20b are O-rings formed of a rubber for preventing leakage of air. As the membranes 19a and 19b, there may be suitably used a polytetrafluoroethane resin sheet which permits a gas to pass therethrough but prevents a liquid from passing therethrough.

The holder 21 is provided with a gas inlet connected to a gas inlet conduit 23a and with a gas outlet 24 connected to the oxidizing zone 2 (not shown) through a gas conduit 24a. The gas inlet conduit 23a is connected to a source (not shown) of a gaseous medium through a pump (not shown), so that by the operation of the pump the gaseous medium is passed successively through the conduit 23a, the inlet 23, the gas permeable disc 18, the outlet 24 and the conduit 24a to the oxidizing zone 2.

Thus, when the holder 21 is immersed in the aqueous medium to be measured, vapors of the organic chlorine compound penetrate through the membranes 19a and 19b into the disc 18 and are carried with the gaseous medium to the oxidizing zone where the the organic chlorine compound is oxidized to form the reactive gas in the same manner as described with reference to FIG. 1.

Figure 4:
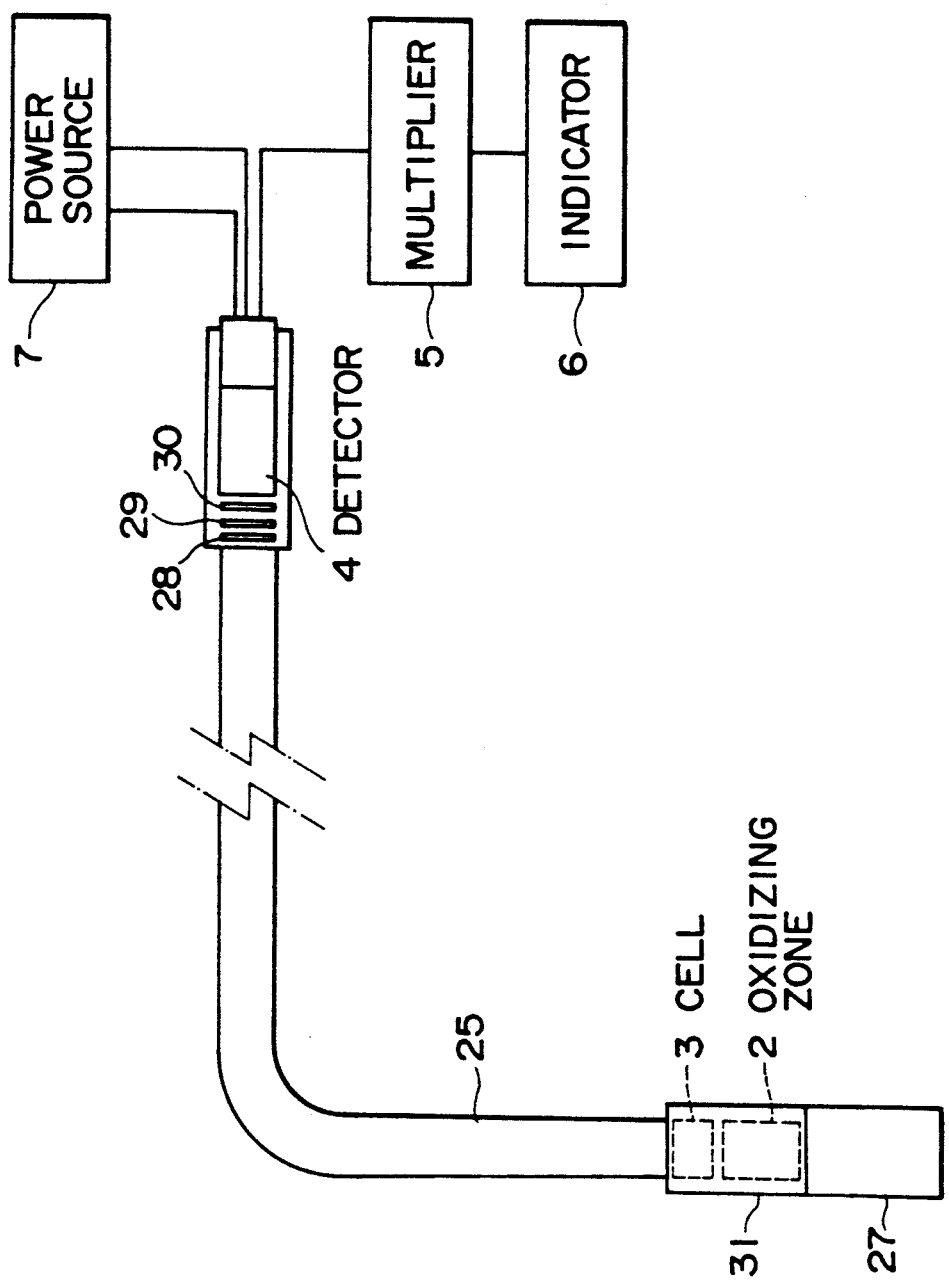
FIG. 4 is a schematic representation of a further embodiment according to the present invention.

Another embodiment of a device for the measurement the concentration of an aqueous medium is shown in FIG. 4 in which the same component parts as in the foregoing embodiments are designated by similar reference numerals. In this embodiment, a bundle of optical fibers 25 is interposed between a chemiluminescent cell 3 and a detector 4 to transmit the light, emitted by chemiluminescence, from the cell 3 to the detector 4 therethrough. The oxidizing zone 2 and the cell 3 are disposed within a tubular housing member 31 connected to one end of the optical fiber 25.

The other end of the optical fiber 25 is connected to the detector 4 through a light controlling member composed of a diaphragm 28, a shutter and an optical filter 30. The light controlling member serves to cut interfering light, such as light emitted from the platinum filament, to minimize measurement errors. Since the majority of the light emitted from the platinum filament has a wavelength of 500 nm or more, and since the wavelength of the light emitted by the chemiluminescence in the cell ranges from 390 to 600 nm, the light controlling member is so selected as to block light of a wavelength of 500 nm or more.

Figure 5:
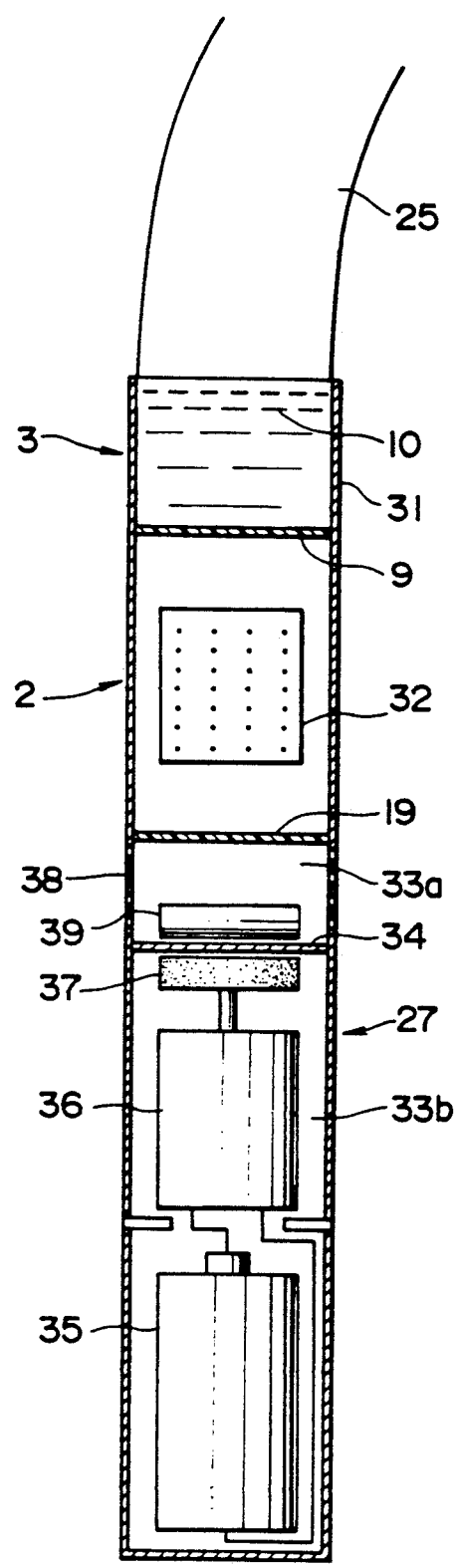
FIG. 5 is a fragmentary, enlarged, cross-sectional view showing the essential part of the apparatus of FIG. 4.

FIG. 5 illustrates the essential part of the device of FIG. 4. A gas permeable membrane 19 is disposed in the tubular housing member 31 to partition the inside space thereof into a first chamber in which the oxidizing zone 2 and the cell 3 are disposed and a second chamber in which a stirrer 27 is disposed.

Provided in the first chamber is a gas permeable membrane 9 by which the first chamber is divided into the oxidizing zone 2 and a cell chamber 10 containing a solution of a chemiluminescent compound. A porous support 32 carrying an oxidizing agent is fixed within the oxidizing zone 2.

The second chamber is divided by a partition plate 34 into an upper chamber 33a in which a magnet bar 39 covered with a polytetrafluoroethylene resin is accommodated and a lower chamber 33b in which a motor 36, a battery 35 for actuating the motor 36 and a magnet 37 connected to the axis of the motor 36 and adapted to rotate by the driving of the motor 36 are disposed. A plurality of openings 38 are formed in the tubular housing member 31 at position of the upper chamber 33a so that the upper chamber 33a is in fluid communication with the outside of the housing member 31.

As a result of the above construction, when the housing member 31 is immersed in the aqueous medium, the aqueous medium is introduced into the upper chamber 33a. The organic chlorine compound contained in the aqueous medium diffuses into the oxidizing zone 2 through the membrane 19 and oxidized therein to form the reactive gas which, in turn, diffuses into the chemiluminescent solution in the cell 3 through the membrane 9. By actuating the motor 36, the magnet bar 39 is rotated to facilitate the introduction of fresh aqueous medium into the upper chamber 33a.

Figure 6:
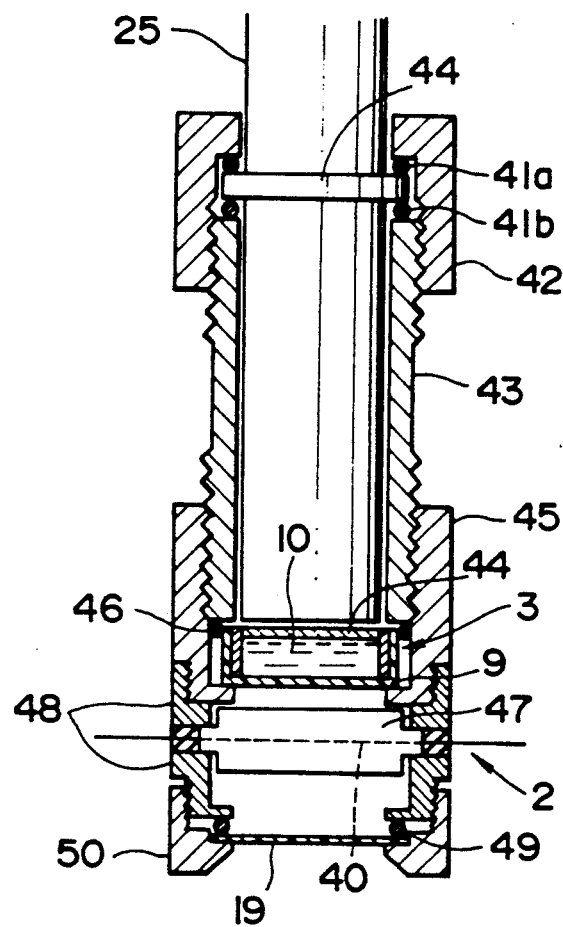
FIG. 6 is a fragmentary, enlarged, cross-sectional view showing the essential part of a further embodiment of the present invention.

FIG. 6 shows another embodiment of the structure of oxidizing zone and chemiluminescent cell suitably applied to the device of FIG. 4. The optical fiber 25 has an end portion fitted with a cylindrical body 43. The cylindrical body 43 is secured to the optical fiber 25 with a cap nut 42 through a flange portion 44 of the optical fiber 25 and a pair of O-rings 41a and 41b. Connected with a cap nut 45 to the tip end of the cylindrical body 43 is a cell 3 containing a chemiluminescent liquid. The upper side of the cell 3 is formed of a glass while the lower side of the cell 3 is formed of a gas permeable membrane 9.

Threadingly connected to the cap nut 45 is a tubular body 48 within which an oxidizing zone 2 is formed. In the tubular body 48 a semicylindrical ceramic cover 47 having a U-shaped cross section is secured with its longitudinally extending opening being oriented downward. A platinum filament 40 is mounted in the ceramic cover 47. The cover 47 serves to prevent the light emitted from the filament 40 from entering the optical fiber 25. Both ends of the filament 40 are connected to watertight lead wires which extend out through the tubular body 48. The lower end of the tubular body 48 is closed with a gas permeable membrane 19 secured to the tubular body 48 with a cap nut 50 through an O-ring 49.

Thus, when the tip end portion of the optical fiber is immersed in the aqueous medium, the organic chlorine compound contained in the aqueous medium diffuses into the oxidizing zone 2 through the membrane 19 and oxidized therein upon contact with the heated platinum filament 40 to form molecular chlorine which, in turn, diffuses into the chemiluminescent solution in the cell 3 through the membrane 9.

The intensity of the light emitted in the cell 3 by chemiluminescence is detected by the detector 4. By previously preparing a calibration curve using samples with known content of an organic chlorine compound, it is possible to determine the concentration of the organic chlorine compound contained in the aqueous or atmospheric medium from the measured values in the detector 4.

Since, in the present invention, the organic chlorine compound contained in an aqueous medium is separated therefrom as vapors, chlorinated olefins (e.g. trichloroethylene and tetrachloroethylene) and chlorinated paraffins (e.g. chloroform and carbon tetrachloride), which are volatile in nature, are suitably measured.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A method of measuring the concentration of an organic chlorine compound contained in a gaseous medium, comprising the steps of:
   feeding said gaseous medium and an oxidizing agent selected from the group consisting of a mixture of $H_2SO_4$ with $NaNO_3$, a mixture of $H_2SO_4$ with $HNO_3$, a mixture of $H_2SO_4$ with $PbO_2$ and $NaNO_3$ and a mixture of $H_2SO_4$ with $PbO_2$ and $NHO_3$ to a reaction zone at a predetermined feed rate and oxidizing the chlorine compound fed to said reaction zone to produce a reactive gas containing $NO_2$ and capable of reacting with a chemiluminescent compound to cause chemiluminescence;
   introducing said reactive gas produced in said reaction zone into a cell containing said chemiluminescent compound to bring said reactive gas into contact with said chemiluminescent compound and thereby to cause chemiluminescence; and
   detecting the intensity of the chemiluminescence in said cell.

2. A method as claimed in claim 1, wherein said chemiluminescent compound is luminol.

3. A method of measuring the concentration of an organic chlorine compound contained in an aqueous medium, comprising the steps of:
   vaporizing said organic chlorine compound and causing the vapors of said organic chlorine compound to pass through a gas permeable membrane, thereby to separate said organic chlorine compound from said aqueous medium;

feeding said separated organic chlorine compound and an oxidizing agent selected from the group consisting of a mixture of $H_2SO_4$ with $NaNO_3$, a mixture of $H_2SO_4$ with $HNO_3$, a mixture of $H_2SO_4$ with $PbO_2$ and $NaNO_3$ and a mixture of $H_2SO_4$ with $PbO_2$ and $HNO_3$ to an oxidizing zone and oxidizing said organic chlorine compound fed to said oxidizing zone to produce a reactive gas containing $NO_2$ and capable of reacting with a chemiluminescent compound to cause chemiluminescence;

introducing said reactive gas produced in said oxidizing zone into a cell containing said chemiluminescent compound to bring said reactive gas into contact with said chemiluminescent compound and thereby to cause chemiluminescence; and detecting the intensity of the chemiluminescence in said cell.

4. A method as claimed in claim 3, wherein said chemiluminescent compound is luminol.

* * * * *